United States Patent [19]

Lanagan et al.

[11] Patent Number: 5,731,521
[45] Date of Patent: Mar. 24, 1998

[54] APPARATUS FOR MONITORING HIGH TEMPERATURE ULTRASONIC CHARACTERIZATION

[75] Inventors: Michael T. Lanagan, Woodridge; David S. Kupperman, Oak Park; George A. Yaconi, Berwyn, all of Ill.

[73] Assignee: The United States of America as represented by the Department of Energy, Washington, D.C.

[21] Appl. No.: 542,757

[22] Filed: Oct. 13, 1995

[51] Int. Cl.$^6$ .................................................. G01N 29/18
[52] U.S. Cl. ................................... 73/632; 73/597; 73/602
[58] Field of Search ............................. 73/64.53, 54.41, 73/632, 643, 644, 579, 597, 602; 336/30; 364/506, 508

[56] References Cited

U.S. PATENT DOCUMENTS

| | | | |
|---|---|---|---|
| 3,699,808 | 10/1972 | Ford | 73/579 |
| 3,751,977 | 8/1973 | Schilling, Jr. | 73/579 |
| 4,346,599 | 8/1982 | McLaughlin | 73/597 |
| 4,377,087 | 3/1983 | Rodot | 73/597 |
| 4,879,905 | 11/1989 | Chen | 73/579 |

*Primary Examiner*—Christine K. Oda
*Attorney, Agent, or Firm*—Bradley W. Smith; Mark P. Dvorscak; William R. Moser

[57] ABSTRACT

A method and an apparatus for nondestructive detecting and evaluating changes in the microstructural properties of a material by employing one or more magnetostrictive transducers linked to the material by means of one or more sonic signal conductors. The magnetostrictive transducer or transducers are connected to a pulser/receiver which in turn is connected to an oscilloscope. The oscilloscope is connected to a computer which employs an algorithm to evaluate changes in the velocity of a signal transmitted to the material sample as function of time and temperature.

21 Claims, 6 Drawing Sheets

APPARATUS FOR MONITORING HIGH TEMPERATURE ULTRASONIC CHARACTERIZATION

CONTRACTUAL ORIGIN OF THE INVENTION

The United States Government has rights in this invention pursuant to Contract No. W-31-109-ENG-38 between the U.S. Department of Energy and Argonne National Laboratory.

BACKGROUND OF THE INVENTION

The present invention relates to an ultrasonic apparatus and method used in the heat treatment of high temperature superconductors and other ceramic and composite materials, including metal alloys. In particular, this invention relates to the combination of a sonic conductor and evaluation device and method that can detect and monitor melting, more specifically wherein the core material has a lower melting temperature than the surrounding sheath material.

High temperature superconductors and other ceramic and composite materials, including metal alloys, hold great promise for usage in a number of technologies, including, but not limited to, current leads, cryogenic fluid level sensors, medical diagnostics, maglev trains, power transmission lines and fault current limiters. Generally such applications will require lengths in excess of 1 kilometer. Materials suitable for such applications have been produced by a number of various combinations of pressing and sintering, melt casting and hot pressing. A method for producing such superconductors and other ceramic and composite materials, known as "powder in tube" is well known in the prior art. See U.S. Pat. No. 5,354,535 to Dorris et al. for a discussion of the powder in tube method. However, manufacturing long lengths in a reproducible manner is one of the major challenge faced by manufacturers.

During the fabrication of such materials, particularly those produced by the powder in tube method, the liquid phase is essential in achieving the proper phase development and grain alignment, and subsequent optimization of electrical properties. At the present time, there is relatively little information regarding microstructural changes and the generation and consumption of liquid during the fabrication of such materials.

Currently a number of options exist for monitoring the melting behavior of superconductors and other ceramics and composite materials, including metal alloys, the most common of which is Differential Thermal Analysis (DTA), wherein the difference in dynamic thermal environment between a reference and test material is measured. However, DTA does not allow for in-situ monitoring of such high-temperature materials and composites during processing, instead requiring powder specimens; does not allow for monitoring materials with volatile species, as DTA requires open crucibles; nor does it allow for monitoring liquid-phase consumption and evolution during isothermal conditions.

Other options for monitoring the melting behavior of materials and composites, include the Differential Scanning Calorimeter (DSC) and the High-Temperature Dilatometer. The DSC is similar to DTA in operation and is useful for measuring heats of formation of chemical reactions, while the Dilatometer measures dimensional changes, i.e., thermal expansion and shrinkage, of a material brought about by changes in its environment. While both the DSC and the Dilatometer allow for monitoring liquid-phase consumption and evolution during isothermal conditions, like the DTA, neither apparatus allow for in-situ monitoring of high-temperature materials during processing, nor does it allow for monitoring materials with volatile species.

It is therefore an object of the present invention to provide a non-destructive apparatus and method for monitoring heat treatment of high-temperature superconductors and other ceramic and composite materials including nondestructively detecting liquid formation and consumption during testing and fabrication.

Another object of the present invention is to provide a non-destructive apparatus and method that can be used both in research and production.

Yet another object of the present invention is to allow such monitoring to occur in-situ during processing of such high-temperature superconductors and other ceramic and composite materials.

It is yet another object of the present invention to allow for monitoring liquid-phase consumption and evolution during isothermal (constant temperature) annealing.

A further object of the present invention is to allow for monitoring high-temperature superconductors and other ceramic and composite materials with volatile species.

A final object of the present invention is to provide an apparatus that can be assembled from low cost, commercially available components.

SUMMARY OF THE INVENTION

In one embodiment of the invention, the material is joined to a magnetostrictive transducer by means of a sonic signal conductor with a first and second end. The second end of sonic signal conductor is joined to the material by an adhesive, which may be a ceramic adhesive but may be any high temperature cement or other high temperature adhesive.

The first end of sonic signal conductor is in contact with a magnetostrictive transducer, which is connected by a cable to a pulser, where the first end of the sonic signal conductor lies inside, and is surrounded by, a transducer. The pulser is in turn connected by a cable to oscilloscope, which in turn is connected by cable to a computer. Further, the computer is connected to a front thermocouple and rear thermocouple by means of cables.

In another embodiment of the invention the material is joined to a first and second magnetostrictive transducers by a first and second sonic signal conductors. The first end of the first sonic signal conductor is in contact with the first magnetostrictive transducer, which is connected to the pulser by means of a cable, while the first end of the second sonic signal conductor is in contact with the second magnetostrictive transducer, which is connected to a pulser by means of a cable. The second end of the sonic signal conductors are in contact with the material. The pulser in turn is connected by a cable to an oscilloscope which in turn is connected by a cable to the computer.

DETAILED DESCRIPTION OF THE INVENTION

The time, t, for a sound wave to travel across a composite material member, having a sheath and a core, is inversely proportional to the elastic modulus of the core material. An increase in propagation time is associated with liquid-phase formation. The acoustic velocity of sound can be determined by treating the composite material member as a thin rod. Young's modulus (E) of a powder core can be calculated from the density and velocity of sound data of the composite material to be tested.

$$E = \rho V^2 \qquad (1)$$

where $\rho$ is the density and $V$ is the longitudinal velocity of sound. The Reuss model, constant stress in the two constituents of a composite, is applied to the calculation of the velocity of sound and Young's modulus.

$$1/E_{comp\ material} = f/E_{core\ material} + (1-f)/E_{sheath\ material} \qquad (2)$$

where f is the volume fraction of the core material, (1–f) is the volume fraction of the surrounding sheath material, $E_{core\ material}$ is the Young's modulus of the core material and $E_{sheath\ material}$ is the modulus of the surrounding sheath material.

Elevating the temperature of the material member to a value below the melting point of the sheath and at the liquid phase formation of the core material, a sharp decrease in longitudinal velocity of sound in the core material is noted. This is attributed to the large decrease of the core elastic modulus due to the presence of a liquid phase. Equation (2) can be modified to account for the change in modulus when liquid is formed, where $E = \lambda + 2\mu$:

$$1/(\lambda+2\mu)_{comp\ material} = f/(\lambda+2\mu)_{core\ material} + (1-f)/(\lambda+2\mu)_{sheath\ material} \qquad (3)$$

where $\lambda$ the Lame' constant, $\mu$ the shear modulus and $(\lambda+2\mu)$ is the modulus of elasticity. The term $\mu$ is 0 for liquid. Equation 3 is rewritten, substituting the notation $M_{s,s}$, $M_{s,l}$ for the modulus of elasticity of the composite with solid and liquid cores, respectively. For the liquid core, $\lambda = K_{liquid-core}$ where K is the bulk modulus. For the sheath material and solid core, $E = \lambda + 2\mu$, where E is the Young's modulus, thus:

$$1/M_{s,s} = f/E_{solid-core} + (1-f)/E_{sheath\ material} \qquad (4)$$

$$1/M_{s,l} = f/K_{liquid-core} + (1-f)/E_{sheath\ material} \qquad (5)$$

If K for the liquid phase is not known, we can use Equation 6 for an isotropic solid, $$K = \frac{1}{3}(1-2v) \cdot E \qquad (6)$$

where v is the Poisson ratio. For v=0.23 to 0.28, which is typical for a solid, K=0.62 E to 0.75 E. For an isotropic solid, one can write the equation $\Delta t/t$ as a function of f where t=time.

From Equation 1, it can be shown that the change in elastic modulus during the formation of the liquid phase is approximately twice that of the change in velocity (or transit time t), thus:

$$\Delta M/M_{s,s} = 2 \cdot \Delta V/V = -2 \cdot \Delta t/t = \{K_{liquid-core}[fE_{sheath\ material} + (1-f) \cdot E_{solid-core}]/E_{solid-core}[fE_{sheath\ material} + (1-f) \cdot K_{liquid-core}]\} - 1 \qquad (7)$$

As result, the change in the ultrasonic echo transit time can be predicted from the variation of elastic modulus during the formation of liquid.

Figure 1:
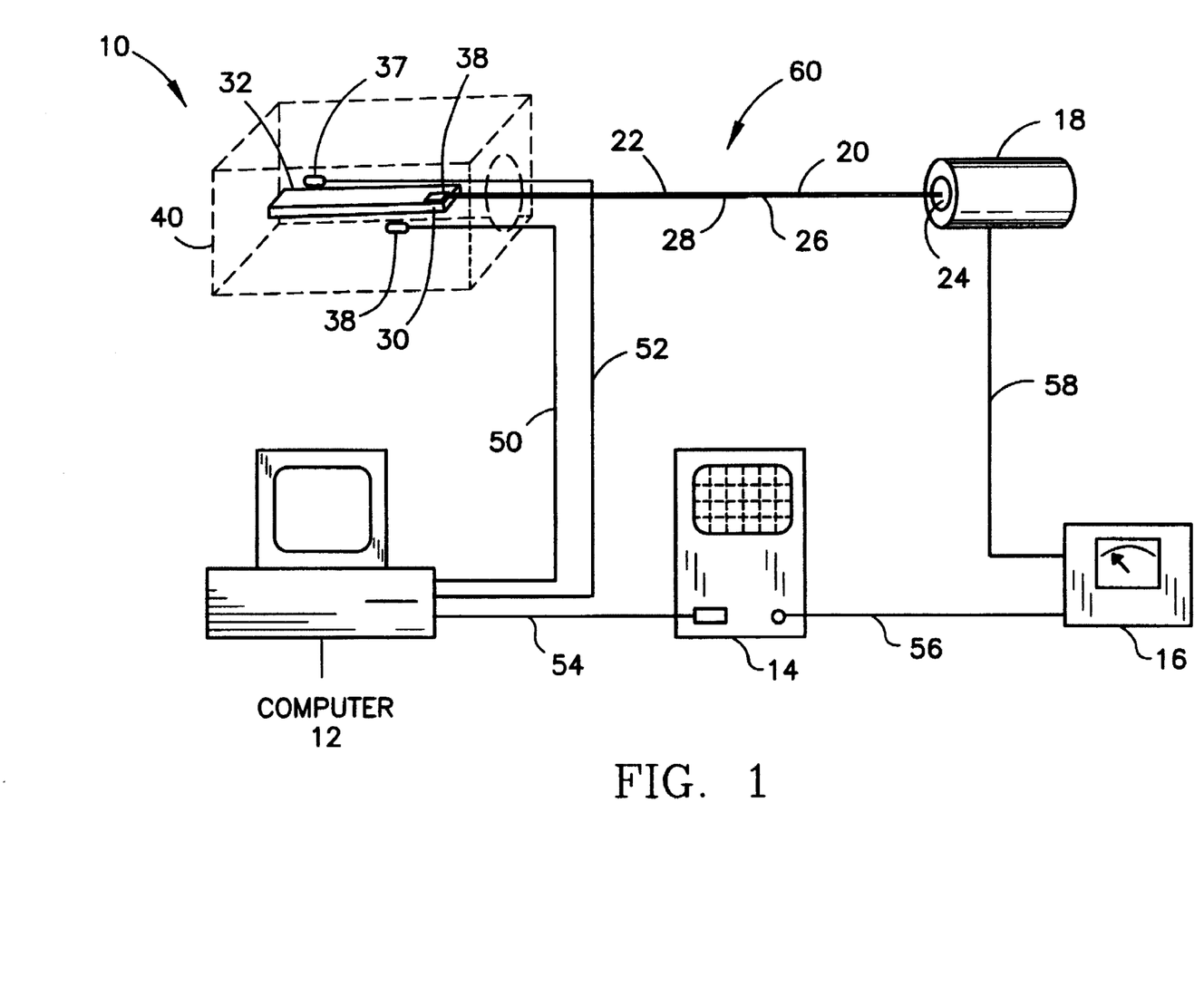
FIG. 1 is a simplified schematic representation of a first embodiment of the invention.
Figure 2:
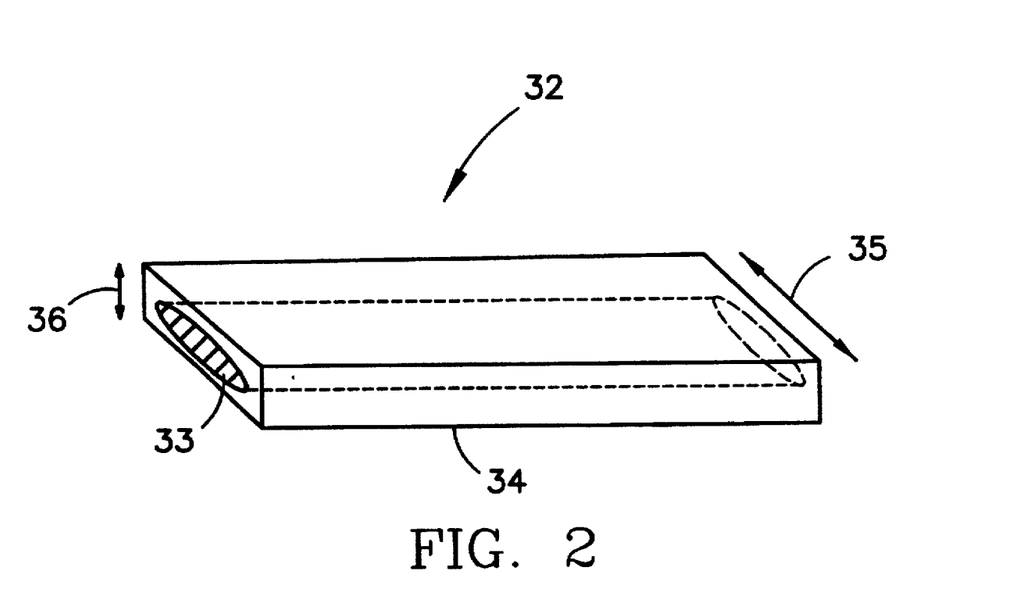
FIG. 2 is a illustration of a portion of a test sample.

In one embodiment of the invention as depicted in FIG. 1, process monitor 10 consists of process unit 40 wherein the monitoring of material 32 is to be undertaken. Material 32 is joined to magnetostrictive transducer 18 by means of sonic signal conductor 60. In the preferred embodiment, sonic signal conductor 60 does not exceed one meter in length and is comprised of inconel rod 22 joined to remendur rod 20, where first end 28 of inconel rod 22 is welded to second end 26 of remendur rod 20 by means of an electronic beam or by any other means which will form a good mechanical bond capable of transmitting a sonic signal. Inconel rod 22 is a commercially available nickel-based, heat- and oxidation-resistant alloy with approximately 13% chromium, 6% iron and small amounts of manganese, silicon and copper. Inconel is used specifically for its heat-resistant properties. Remendur is used specifically for its ability to generate and transmit sonic signals. However, the choice of the inconel and remendur rod is not critical, a ceramic conductor could be utilized as long as it is a good conductor of sound and able to withstand the temperatures of the process. Second end 38 of sonic signal conductor 60 is joined to material 32 by adhesive 30, which in the preferred embodiment is a ceramic adhesive, but may be any high temperature cement or other high temperature adhesive. FIG. 2 more clearly depicts a typical material sample or member 32 having a core test material or composite material 33 surrounded by a sheath 34 of a different material where in the preferred embodiment the sheath 34 has a higher melting temperature than the core 33. In addition, in the preferred embodiment, the width 35 to height 36 ratio is approximately 30, and the member is in the form of a thin ribbon where the height 36 is less than 0.025 in.

Returning to FIG. 1, first end 24 of sonic signal conductor 60 is in contact with magnetostrictive transducer 18, which is connected to pulser/receiver 16 by means of cable 58. In the preferred embodiment, first end 24 lies inside, and is surrounded by, transducer 18. Pulser 16 in turn is connected by cable 56 to oscilloscope 14, which in turn is connected by cable 54 to computer 12. Further, computer 12 is connected to front thermocouple 38 by means of cable 50 and rear thermocouple 37 by means of cable 52.

In operation, such in-situ monitoring and evaluating of material 32 comprises the steps of providing an electrical signal, converting said electrical signal to a sonic signal; transmitting said sonic signal to the material to be evaluated; receiving said sonic signal from said material; converting said sonic signal to an electrical signal; digitizing said electrical signal and evaluating the acoustic-velocity of said sonic signal as a function of temperature. In particular, sonic signal conductor 60 is affixed to material 32, which is then placed in process unit 40. Pulser 16 generates an electrical signal which is transmitted to transducer 18 by means of cable 58. Transducer 18 then launches a sonic signal in a range of between 100 kHz to 150 kHz, nominally 100 kHz, which is transmitted to material 32 by means of sonic conductor 60. Part of the sonic signal is reflected from either end of the material 32. Oscilloscope 14, having the capability to convert analog signals to digital signals, digitizes the electrical signal received from pulser 16 by means of cable 56 and displays it as a function of voltage. The distance between the two echos is called the transit time and is the time it takes the sonic signal to travel through material 32 (velocity of the sonic signal), which is dependant on the microstructure of the material thereof. Said digital signal is transmitted to computer 12 by means of cable 54. Computer 12 records the transit time throughout the process and analysises it utilizing an algorithm written by Applicants, which relates the change in velocity of the sound wave as a function of temperature.

Figure 5:
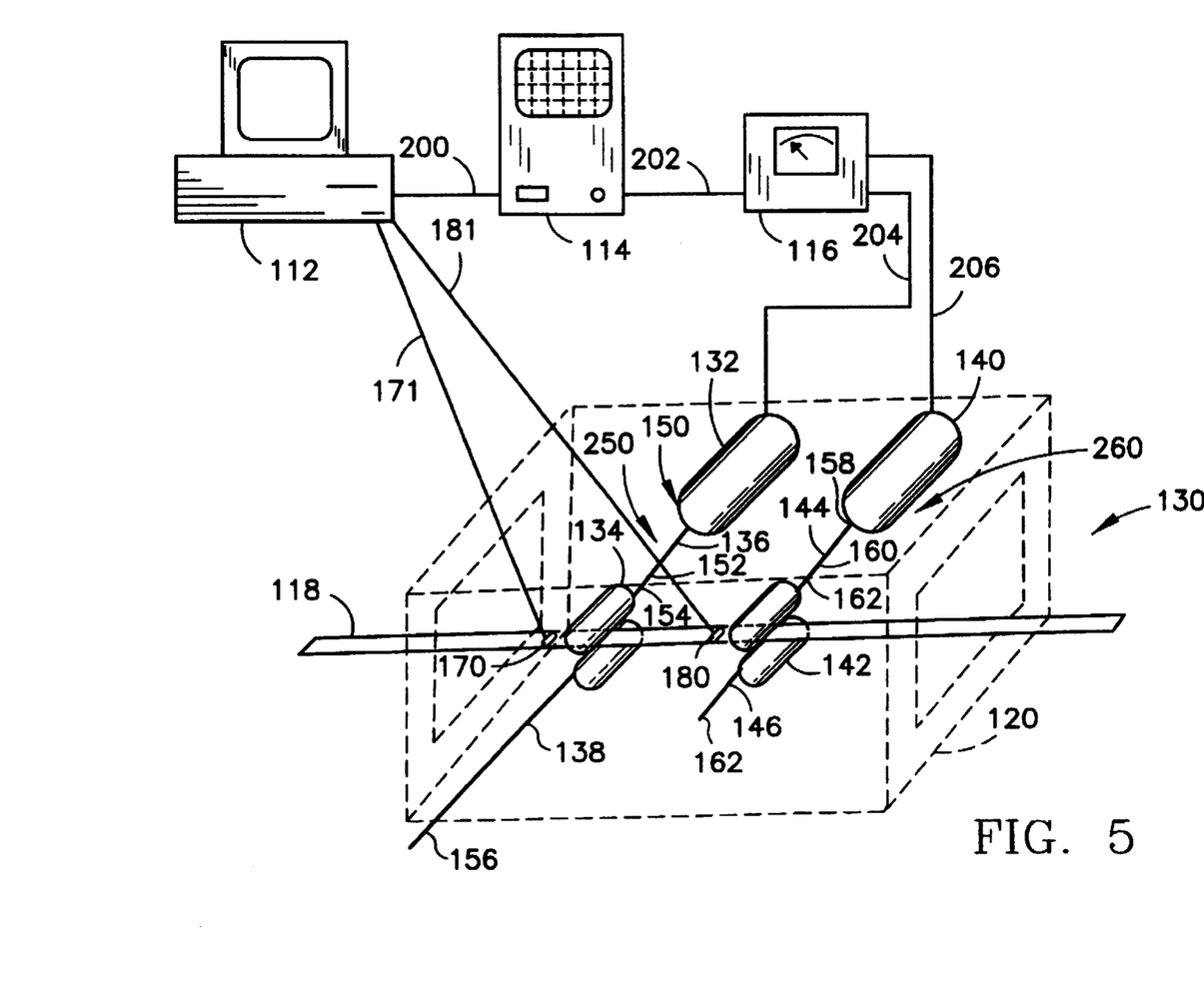
FIG. 5 is a simplified schematic representation of a second embodiment of the invention.

In another embodiment of the invention as depicted in FIG. 5, process monitor 110 consists of process unit 120 wherein the monitoring of material member 118 is to be undertaken. Material 118 is joined to first magnetostrictive transducer 132 by means of first sonic signal conductor 250 and to a second magnetostrictive transducer 140 by means of second sonic signal conductor 260. In the preferred embodiment, sonic signal conductors 250 and 260 do not exceed one meter in length and are comprised of first inconel rod 138 joined to first remendur rod 136 and second inconel rod 146 joined to second remendur rod 144, where first end 154 of inconel rod 138 is welded to second end 152 of first remendur rod 136 and first end 162 of second inconel rod 146 is welded to second end 160 of second remendur rod 144 by means of an electronic beam. Inconel rods 138 and 146 are a commercially available nickel-base, heat- and oxidation-resistant alloy with approximately 13% chromium, 6% iron and small amounts of manganese, silicon and copper. Inconel is used specifically for its hem-resistant properties. Remendur is used specifically for its ability to generate and transmit sonic signals. However, the choice of the inconel and remendur rod are not critical, a ceramic conductor could be utilized as long as it is a good conductor of sound and able to withstand the temperatures of process unit 120. Thermocouple 170, in close proximity to material 118, is connected to computer 112 by connection 171, and thermocouple 180, in close proximity to material 118, is connected to computer 12 by connection 181.

Figure 6:
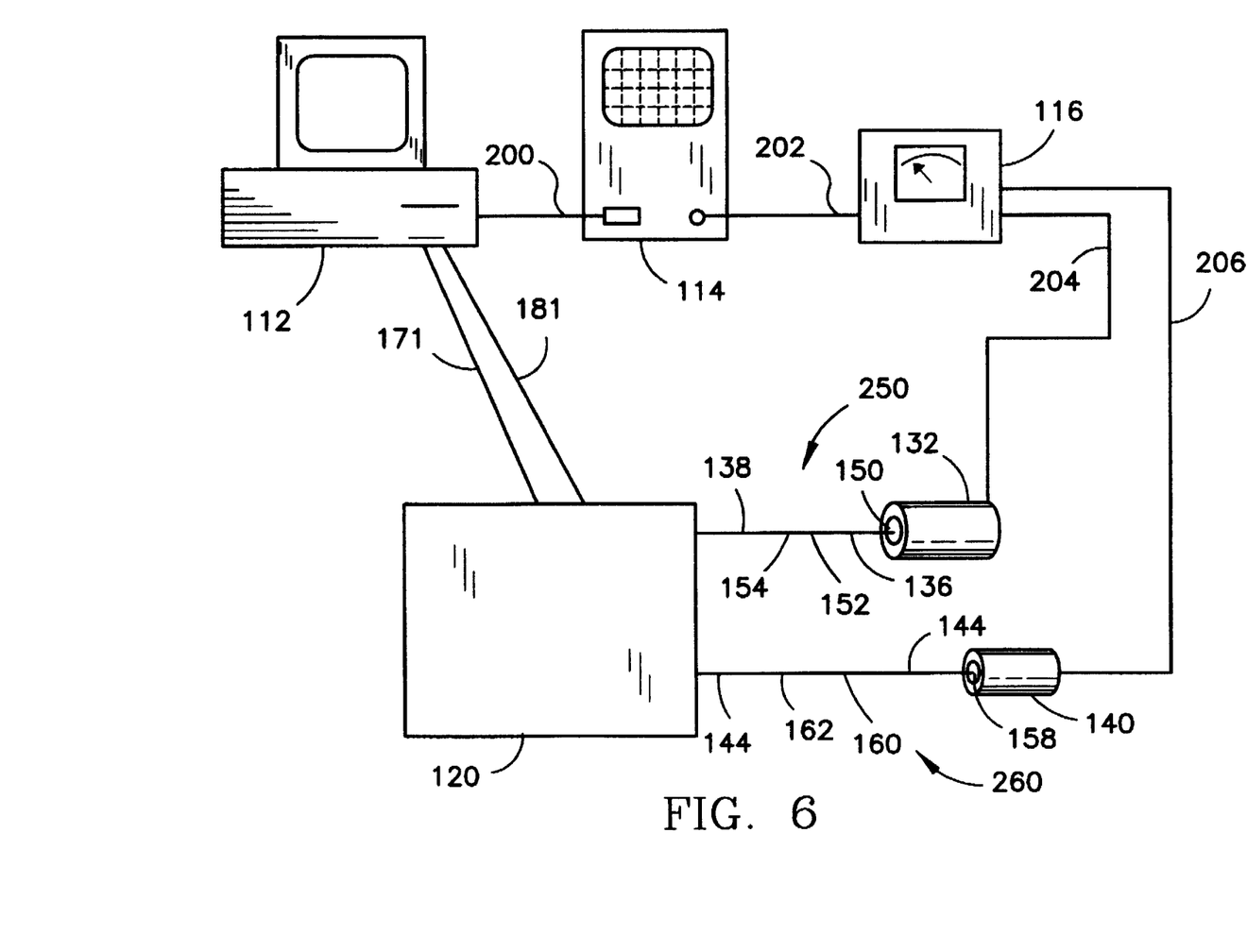
FIG. 6 is a simplified schematic representation of the second embodiment of FIG. 5 depicting the relationship of the transducers and rods to the process unit.

As depicted in FIG. 6, first end 150 of sonic signal conductor 250 is in contact with first magnetostrictive transducer 132, which is connected to pulser 116 by means of cable 204, while first end 158 of sonic signal conductor 260 is in contact with second magnetostrictive transducer 140, which is connected to pulser 116 by means of cable 206. In the preferred embodiment, first ends 150 and 158 lie inside, and are surrounded by transducers 132 and 140 respectively. Pulser 116 in turn is connected by cable 202 to oscilloscope 114, which in turn is connected by cable 200 to computer 112.

Sonic signal conductors 250 and 260 are in contact with material 118 while said material 118 is in process unit 120. In the preferred embodiment, rollers 134 act to keep inconel rod 136 in rolling contact with material 118, while rollers 142 act to keep inconel rod 146 in rolling contact with material 118 while material 118 is in processing unit 120. As further depicted in FIG. 5, remendur rods 136 and 144 do not extend inside processing unit 120, only ends 156 and 162 of inconel rods 138 and 146 respectively, extend therein. However, as provided above, said sonic signal conductors are not limited to the inconel/remendur arrangement described above, any sonic conductor can be used as long as it is a good conductor of sound and withstand the temperatures of the process. Moreover, said sonic conductor need not be in rolling contact with material 118, as long as said conductor is pressed against, and in good mechanical contact with, material 118 such that the sonic signal can be transmitted to and from said material.

In operation, such in-situ monitoring and evaluating material 118 comprises the steps of providing an electrical signal, converting said electrical signal to a sonic signal; transmitting said sonic signal to the material to be evaluated; receiving said sonic signal from said material; converting said sonic signal to an electrical signal; digitizing said electrical signal and evaluating the acoustic-velocity of said sonic signal as a function of time. In particular this involves placing material 118 in process unit 120, wherein pulser 116 generate an electrical signal that is transmitted to transducer 132 by means of cable 204. Transducer 132 then launches a sonic signal in a range of between 100 kHz to 150 kHz, nominally 100 kHz, which is transmitted to material 118 by means of sonic conductor 250. A higher frequency would cause the waves to attenuate, while a lower frequency would comprise the resolution. The sonic signal travels through material 118 and is transmitted to transducer 140 wherein an electrical signal is generated. Said electrical signal is transmitted to pulser 116 by means of cable 202 and then to oscilloscope 114 by means of cable 202. Oscilloscope 114, having the capability to convert analog signals to digital signals, digitizes the electrical signal and displays it as a function of voltage. The transit time and is the time it takes the sonic signal to travel through material 118 (velocity of the sonic signal) and it is dependant on the microstructure of the material thereof. Said digital electrical signal is then transmitted to computer 112 by means of cable 200. Computer 112 records the transit time throughout the process and analysises it utilizing an algorithm written by Applicants, which relates the change in velocity of the sound wave as a function of temperature.

Figure 3:
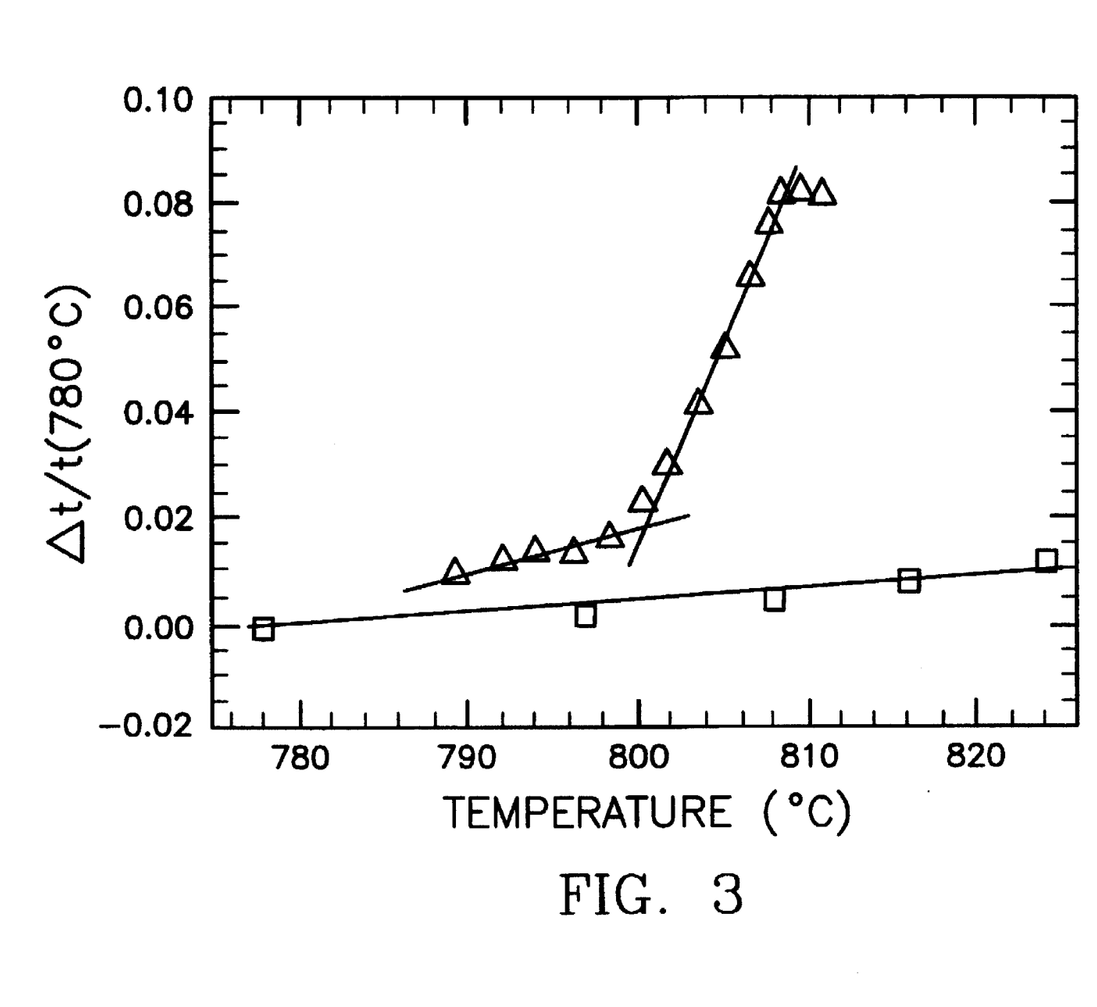
FIG. 3 is graphic representation of the ultrasonic echo transit time for materials containing Ag-clad NaCl and Ag-clad alumina tapes.

As provided above, an increase in propagation time is associated with liquid-phase formation. FIG. 3 is a graphical depiction of an ultrasonic echo transit time for an Ag-clad NaCl tape (triangles in FIG. 3). An increase in propagation time is associated with liquid-phase formation. The melting point of the NaCl core material is shown at the intersection of the two lines. An Ag-clad alumina tape is shown for comparison (squares in FIG. 2). No melting is expected at the temperatures used, and no acoustic velocity change is observed.

Figure 4:
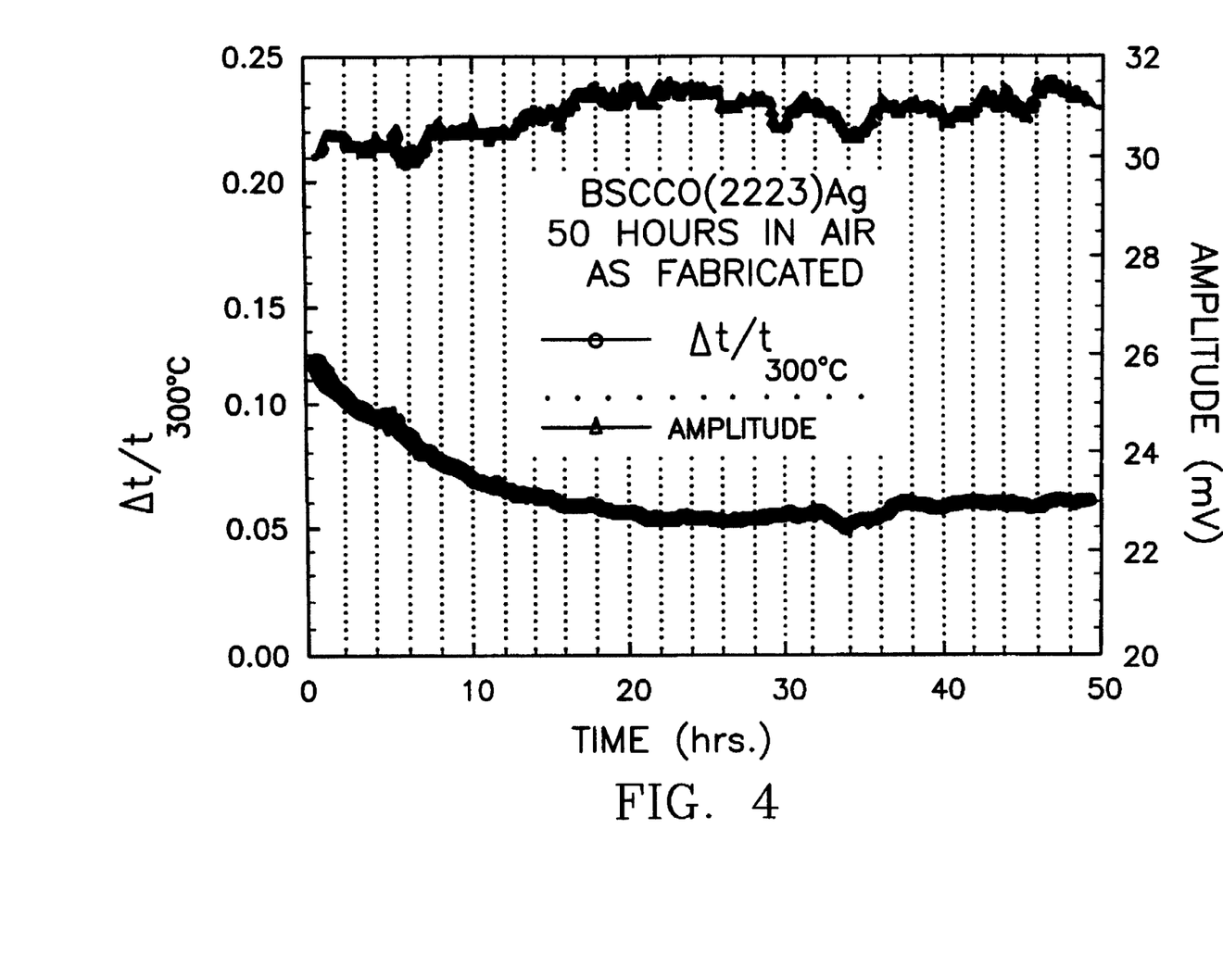
FIG. 4 is a graphic representation of the echo transit time and amplitude as a function of heat-treatment time for a BSCCO/Ag composite material at 845° C. in 21% $O_2$.

FIG. 4 is a graphical representation of the consumption of liquid as a function of time for a fixed temperature BSCCO (core)/Ag(sheath) composite material sample. After choosing the optimal temperature for fabrication is selected, generally a few degrees above the temperature at which the liquid phase appears to form, the consumption of liquid can be monitored. The lower curve in FIG. 3 depicts the decrease in transit time as a function of time at a constant temperature (845° C.). The upper curve depicts the echo amplitude vs. time which is relatively stable.

EXAMPLE

The following non-limiting example demonstrates certain aspects of the method and apparatus of the invention.

The technique was validated by using sodium chloride and alumina core materials. In FIG. 3, the change in propagation time $\Delta t(=t-t\ 780°\ C.)$ is normalized to the time between echoes at 780° C. The melting point can be determined by taking the intersections of the lines above and below the transition.

Young's modulus (E) of a powder core can be calculated from the density and velocity of sound data of the material to be tested.

$$E = \rho V^2 \quad (1)$$

where $\rho$ is the density and V is the longitudinal velocity of sound. The Reuss model is applied to the calculation of the velocity of sound and Young's modulus.

$$1/E_{NaCl/Ag} = f/E_{NaCl} + (1-f)/E_{Ag} \quad (2)$$

Equation (2) can be modified to account for the change in modulus when liquid is formed, where $E=\lambda+2\mu$:

$$1/(\lambda+2\mu)_{NaCl/Ag} = f/(\lambda+2\mu)_{NaCl} + (1-f)/(\lambda+2\mu)_{Ag} \quad (3)$$

where $\lambda$ is the Lame' constant, $\mu$ the shear modulus and $(\lambda+2\mu)$ is the modulus of elasticity. The term $\mu$ is 0 for liquid. Equation 3 is rewritten, substituting the notation $M_{s,s}$ and $M_{s,l}$ for the modulus of elasticity of the composite with solid and liquid cores, respectively. For the liquid core, $\lambda=K_{liquid-core}$ where K is the bulk modulus. For the sheath material and solid core, $E=\lambda+2\mu$, where E is the Young's modulus, thus:

$$1/M_{s,s} = f/E_{solid-NaCl} + (1-f)/E_{Ag} \quad (4)$$

$$1/M_{s,l} = f/K_{liquid-NaCl} + (1-f)/E_{Ag} \quad (5)$$

If K for the liquid phase is not known, we can use Equation 6 for an isotropic solid, $$K = 1; 3(1-2v) \cdot E \quad (6)$$

where v is the Poisson ratio. For $v=0.23$ to 0.28, which is typical for a solid, $K=0.62$ E to 0.75 E. For an isotropic solid, the equation $\Delta t/t$ as a function of f can then be written.

From Equation 1, it can be shown that the change in elastic modulus during the formation of the liquid phase is approximately twice that of the change in velocity (or transit time t), thus:

$$\Delta M/M_{s,s} = 2 \cdot \Delta V/V = -2 \cdot \Delta t/t = \{K_{liquid-NaCl}[f \cdot E_{Ag} + (1-f) \cdot E_{solid-NaCl}]/E_{s-solid-NaCl}[f \cdot E_{Ag} + (1-f) \cdot K_{liquid-NaCl}]\} - 1 \quad (7)$$

The velocity of sound using the above described apparatus was used to establish the room temperature modulus of silver at 70.91 GPa, which is consistent with the literature of 71 GPa.

Although the present invention has been described hereinabove in reference to the sending of a sonic signal through a transducer and sonic signal coupler, the invention is not so limited. The invention is directed to the improved means of monitoring microstructural changes of materials during high temperature processing. The sonic signal may be a pulsing or non-pulsing sonic signal.

In light of the foregoing disclosure, further alternative embodiments of the present invention will undoubtedly suggest themselves to those skilled in the art. It is thus intended that the disclosure be taken as illustrative only, and that it not be construed in any limiting sense. Modifications and variations may be resorted to without departing from the spirit and the scope of this invention, such modifications and variations are considered to be within the purview and the scope of the appended claims.

The embodiments of the invention in which an exclusive property or privilege is claimed are defined as follows:

1. An apparatus for the nondestructive detection and evaluation of microstructural changes including liquid phase formation and consumption in a material during processing, comprising:
    a signal initiation means for initiating a signal to test for said microstructural changes in said material and for processing a response to said signal;
    a transducer means responsive to said signal initiation means where said transducer means initiates a test signal;
    a transmission member where a first contact area of said transmission member is in contact with a test sample of said material and a second contact area of said transmission member is coupled to said transducer means in such a manner that said transmission member is capable of conducting said test signal from said transducer means to said test sample and conducting a responsive echo signal from said transducer means to said transducer means and where said transducer means is responsive to said echo signal;
    thermocouple means for measuring a temperature associated with said test sample where said thermocouple means is in close proximity to specific portions of said test sample;
    a data evaluation means where said data evaluation means is electrically coupled to said signal initiation means and said thermocouple means and where said data evaluation means processes a first data stream from said thermocouple means and a second data stream from said signal initiation means to determine sample properties;
    heating means for heating the test sample to a temperature above ambient temperature; and
    an enclosure means for enclosing said heating means, said thermocouple means, said sample, and a portion of said transmission member.

2. The apparatus of claim 1 where said test sample is an elongated member having a core of the material surrounded by a sheath of a different material where said sheath is a solid and where said core melts at a lower temperature than said sheath.

3. The apparatus of claim 2 where said sheath of said test sample is shaped like a rod.

4. The apparatus of claim 2 where said sheath is shaped in the form of an extended ribbon.

5. The apparatus of claim 4 where said transducer means is made up of two transducers each coupled to a distinct transmission member and where each of said transmission members is in contact with said test sample at a specified spacing with respect to each other and where said ribbon is in the form of a continuous ribbon moving through said enclosure means.

6. The apparatus of claim 5 where each of said transmission members is coupled to a roller which is in contact with said ribbon of test material.

7. The apparatus of claim 1 where said transducer means is a magnetostrictive transducer which converts an electrical signal to a sonic signal and reciprocally converts an echo sonic signal to an echo electrical signal.

8. The apparatus of claim 7 where said sonic signal has a frequency in the range of 100 kHz to 150 kHz.

9. The apparatus of claim 1 where said transmission member means is a good conductor of sonic waves and is able to withstand said temperature of said heating means.

10. The apparatus of claim 1 where said signal initiation means is a pulser/receiver which transmits a pulse signal to said transducer means and receives an response signal from said transducer means in response to said echo signal.

11. The apparatus of claim 10 where said signal initiation means also includes a means for digitizing said response signal and transmitting said digitized signal to said data evaluation means.

12. The apparatus of claim 1 where said data evaluation means is a computer which is programmed to track said echo signals with respect to test sample temperature and time.

13. The apparatus of claim 1 where said transducer means is a single transducer capable of generating a sonic signal and receiving a response signal from said test sample.

14. The apparatus of claim 1 where said data evaluation means includes a device to convert an analog signal to a digital signal which is then processed by a computer.

15. An apparatus for nondestructive detecting and evaluating microstructural changes including liquid phase formation and consumption in a material during processing, comprising:

a signal initiation means for initiating a signal to test for said microstructural changes in said material and processing a response to said signal;

a transducer means responsive to said signal initiation means where said transducer means initiates a test signal in a transmission member means, where said transmission member means is coupled to a test sample, containing said material, in such a manner as to be capable of transmitting said test signal to said test sample and transmitting a responsive echo signal back to said transducer, and where said transducer means is responsive to said echo signal and where said transmission member is a good conductor of sonic waves and is able to withstand heating to an elevated temperature and where said transmission means is formed from a remendur rod joined to a inconel rod where said remendur rod is coupled to said transducer and said inconel rod is bonded to said test sample;

thermocouple means for measuring a temperature associated with said test sample where said thermocouple means is in close proximity to specific portions of said test sample, where said thermocouple means is electrically coupled to a data collection means, and where said data collection means is coupled to said signal initiation means; and heating means for heating the test sample to a temperature above ambient temperature.

16. An apparatus for nondestructive detecting and evaluating a microstructural changes including liquid phase formation and consumption in a material during processing at temperatures above room temperature comprising:

a signal initiation means for initiating a signal to test for said microstructural changes in said material and processing a response to said signal;

a transducer means responsive to said signal initiation means where said transducer means initiates a test signal in a transmission member means, where said transmission member means is in physical contact with a test sample containing said material in such a manner as to be capable of conducting said test signal to said test sample, and where said transducer means is responsive to a plurality of echo signals generated in said test sample in response to said test signal and conducted from said test sample to said transducer by means of said transmission means;

thermocouple means for measuring a temperature associated with said test sample where said thermocouple means is in close proximity to the test sample;

heating means for heating the test sample to a temperature above ambient temperature;

an enclosure which encloses said heating means, said thermocouple means, part of said transmission member means, and the portion of said test sample undergoing testing;

evaluation means for evaluating a data response from said test sample and a response from said thermocouple to determine liquid formation and consumption where said evaluation means is coupled to said signal initiation means and said thermocouple means and which includes a programmable computer capable of analyzing said sample response data and said thermocouple response data.

17. The apparatus of claim 16 where said test sample is an elongated member having a core of the material surrounded by a solid sheath of a different material where said core of said test sample melts at a lower temperature than that of said sheath.

18. The apparatus of claim 17 where said core of said test sample melts at a lower temperature than that of said sheath.

19. The apparatus of claim 16 where said transducer means is a magnetostrictive transducer which converts an electrical signal to a sonic signal and reciprocally converts a echo sonic signal to a echo electrical signal.

20. The apparatus of claim 16 where said transducer means is made up of two transducers each coupled to a distinct transmission member, where each transmission member is in contact with a test sample having a core and an outer sheath shaped in the form of a ribbon, where the transmission members are spaced at a specified distance with respect to each other, and where said ribbon is in the form of a continuous ribbon moving through the enclosure means.

21. The apparatus of claim 20 where each of said transmission members is coupled to a roller which is in contact with said ribbon of said test material.

\* \* \* \* \*